US011173264B2

(12) United States Patent
    Nitta

(10) Patent No.: US 11,173,264 B2
(45) Date of Patent: Nov. 16, 2021

(54) RESPIRATORY ASSISTANCE PROGRAM AND RESPIRATORY ASSISTANCE DEVICE

(71) Applicant: Metran Co., Ltd., Kawaguchi (JP)

(72) Inventor: Kazufuku Nitta, Saitama (JP)

(73) Assignee: Metran Co., Ltd., Kawaguchi (JP)

( * ) Notice: Subject to any disclaimer, the term of this patent is extended or adjusted under 35 U.S.C. 154(b) by 311 days.

(21) Appl. No.: 16/322,660

(22) PCT Filed: Aug. 3, 2017

(86) PCT No.: PCT/JP2017/028167
    § 371 (c)(1),
    (2) Date: Feb. 1, 2019

(87) PCT Pub. No.: WO2018/025950
    PCT Pub. Date: Feb. 8, 2018

(65) Prior Publication Data
    US 2021/0128851 A1     May 6, 2021

(30) Foreign Application Priority Data
    Aug. 3, 2016 (JP) .............................. JP2016-152669

(51) Int. Cl.
    *A61M 16/00*     (2006.01)

(52) U.S. Cl.
    CPC ...... *A61M 16/024* (2017.08); *A61M 16/0066* (2013.01); *A61M 2205/3331* (2013.01);
    (Continued)

(58) Field of Classification Search
    CPC .............. A61M 16/00; A61M 16/0057; A61M 16/0066; A61M 16/0069; A61M 16/021;
    (Continued)

(56) References Cited

U.S. PATENT DOCUMENTS

| 3,961,627 A | 6/1976 | Ernst et al. |
| 5,535,738 A * | 7/1996 | Estes ................ A61M 16/024 |
| | | 128/204.21 |

(Continued)

FOREIGN PATENT DOCUMENTS

| EP | 2564887 A2 | 3/2013 |
| EP | 2564887 A3 | 1/2018 |

(Continued)

OTHER PUBLICATIONS

International Search Report issued in PCT/JP2017/028167, dated Nov. 7, 2017.

(Continued)

*Primary Examiner* — Joseph D. Boecker
(74) *Attorney, Agent, or Firm* — Flynn Thiel, P.C.

(57) ABSTRACT

A program for controlling a respiratory assistance device that is connected to a user's airway and regulates an airway pressure to assist ventilation has a plurality of different respiratory assistance modes. The respiratory assistance program causes a computer to realize an input reception function that receives an input of setting for a respiratory assistance mode during operation of an air blower that blows air to the user's airway, and a flow rate control function that, when the input reception function receives the input of setting, controls a flow rate from the air blower in reflection of a result of the input of setting. A respiratory assistance device in which a user can change setting to select a comfort pressure and flow rate is provided by using such a program.

15 Claims, 9 Drawing Sheets

(52) U.S. Cl.
CPC .............. *A61M 2205/3334* (2013.01); *A61M 2205/502* (2013.01)

(58) Field of Classification Search
CPC .............. A61M 16/022; A61M 16/024; A61M 2205/3344; A61M 2205/502
See application file for complete search history.

(56) References Cited

U.S. PATENT DOCUMENTS

| | | | | |
|---|---|---|---|---|
| 2001/0027791 | A1* | 10/2001 | Wallace | A61M 16/024 128/204.21 |
| 2002/0077856 | A1* | 6/2002 | Pawlikowski | G16H 40/40 705/2 |
| 2002/0088465 | A1* | 7/2002 | Hill | A61M 16/026 128/204.23 |
| 2004/0016433 | A1* | 1/2004 | Estes | A61M 16/0051 128/204.21 |
| 2008/0185009 | A1* | 8/2008 | Choncholas | A61M 16/00 128/897 |
| 2009/0205662 | A1* | 8/2009 | Kwok | A61M 16/0069 128/204.23 |
| 2010/0108064 | A1* | 5/2010 | Blackwell | A61M 16/0057 128/204.21 |
| 2011/0220107 | A1* | 9/2011 | Kimm | A61M 16/00 128/204.21 |
| 2011/0232643 | A1* | 9/2011 | Mechlenburg | A61M 16/021 128/204.23 |
| 2012/0096381 | A1 | 4/2012 | Milne et al. | |
| 2012/0192867 | A1* | 8/2012 | Lewis | A61M 16/0051 128/204.21 |
| 2012/0291785 | A1* | 11/2012 | Ramanan | A61M 16/0006 128/204.23 |
| 2013/0055134 | A1* | 2/2013 | Knor | A61M 16/0057 715/771 |
| 2013/0239961 | A1* | 9/2013 | Ross, Jr. | A61M 16/0057 128/202.22 |
| 2014/0020688 | A1* | 1/2014 | Sibenaller | A61M 16/026 128/204.23 |
| 2015/0250963 | A1 | 9/2015 | Ramanan et al. | |
| 2016/0015918 | A1 | 1/2016 | Kuriger et al. | |
| 2016/0339201 | A1 | 11/2016 | Nitta | |
| 2017/0007174 | A1* | 1/2017 | Colbaugh | A61B 5/0816 |

FOREIGN PATENT DOCUMENTS

| | | |
|---|---|---|
| JP | 2008-67941 A | 3/2008 |
| JP | 2014-509224 A | 4/2014 |
| JP | 2015-142646 A | 8/2015 |
| WO | 0226283 A2 | 4/2002 |
| WO | 0226283 A3 | 4/2002 |
| WO | 2008/100859 A2 | 8/2008 |
| WO | 2010070498 A1 | 6/2010 |
| WO | 2011057362 A1 | 5/2011 |
| WO | 2011057362 A4 | 5/2011 |
| WO | 2013/067580 A1 | 5/2013 |
| WO | 2015125037 A1 | 8/2015 |
| WO | 2015136430 A1 | 9/2015 |

OTHER PUBLICATIONS

Written Opinion issued in PCT/JP2017/028167, dated Nov. 7, 2017.
Website URL: http://www.metran.co.jp/products/products2/190.html; date of retrieval: May 31, 2016; Metran Co., Ltd > Products > Jusmine.
Certification for Exception to Loss of Novelty filed in PCT/JP2017/028167; Publication: "The front line development of CPAP apparatus"; Publication date: Jul. 20, 2016; Publisher: Metran Co., Ltd. Tran Ngog Phuk (Kazuhuku Nitta).
European Search Report corresponding to European Application No. 17837051.6, dated Nov. 15, 2019 (7 pages).
BleaseSirius Anesthesia Systems User Manual 073-0212-00/REV. B dated Dec. 2010, retrieved on Aug. 26, 2015 (258 pages).
European Office Action issued in corresponding European Application No. 17 837 051.6, dated Jul. 21, 2020 (10 pages).

* cited by examiner

RESPIRATORY ASSISTANCE PROGRAM AND RESPIRATORY ASSISTANCE DEVICE

TECHNICAL FIELD

The present invention relates to a continuous positive airway pressure respiratory therapy device.

BACKGROUND ART

Sleep apnea syndrome (SAS) is caused by descent of a root of a tongue and a soft palate due to relaxed muscles of an airway during sleep, which clogs the airway. The number of potential patients of SAS in Japan is conceivable to be 3 million or more. SAS patients have 2 to 4 times the normal risk for developing a circulatory disease, higher possibilities for a sleep disorder resulting in heavy drowsiness, and 2 or more times the normal risk for having a traffic accident. For such patients, continuous positive airway pressure (CPAP) therapy is effective which utilizes respiratory assistance devices (refer to Patent Literature 1 and Non-Patent Literature 1) that are provided with an air blower for applying a positive pressure to the airway. The respiratory assistance device feeds compressed air supplied from the air blower to the patient's airway.

FIG. 8 is an explanatory view of usage of a conventionally respiratory assistance device (CPAP) 1. A user wears a mounting section 4, such as a mask for covering his or her nose and mouth or a nasal mask for covering only his or her nasal cavities. The mounting section 4 is fixed on his or her head with a mounting section fixing tool 5. Maintaining a positive pressure into an airway during sleep prevents clogging of the airway. A control unit 2 is generally provided with an air blower, a humidifier and the like. Compressed air is supplied through an air tube 3, and fed from the mounting section 4 into the user's airway.

The CPAP is broadly divided into two types. One is a fixed pressure type (refer to FIG. 9A) in which a constant pressure is kept applied into the user's airway. The other is a so-called Auto-CPAP type (refer to a solid line in an upper graph of FIG. 9C) in which pressure variation in the mounting section 4 due to breathing of the user is detected and compressed air is fed at an appropriate flow rate in synchronization with expiratory and inspiratory timing. In either type, effects on breathing, pulses, blood pressure and the like are measured using a polygraph, which records a breathing state during sleep, in the presence of a doctor, and the doctor formulates a set pressure value (called prescribed pressure). Applying the prescribed pressure to the airway during sleep prevents clogging of the airway, so that sleep apnea syndrome is thereby treated (refer to, for example, Patent Literature 1, i.e., Japanese Patent Application Laid-Open No. 2015-142646 and Non-Patent Literature, i.e., a website (URL: http://www.metran.co.jp/products/products2/190.html) [date of retrieval: May 31, 2016] of Metran Co., Ltd., [online], Products>Jusmine).

The conventional respiratory assistance devices (CPAP) are variously devised to facilitate users' breathing and improve the users' comfort. For example, there is a drawback that applying a positive pressure during exhaling makes exhalation difficult and hence makes breathing difficult. To overcome this drawback, a method has been devised in which pressure variation in accordance with exhalation is detected by a pressure sensor, and a valve (relief valve) attached around the mounting section 4 is opened to prevent an excessive increase in airway pressure and to facilitate breathing (refer to a lower graph of FIG. 9B). A control in the Auto-CPAP type has also been devised in which pressure is slightly reduced in the latter half of an inspiratory period I for performing inhalation in order to prevent feeding air into the airway by constraint, and the pressure is reduced at a first step of an expiratory period E for performing exhalation in order to facilitate the exhalation (refer to a dotted line in a lower graph of FIG. 9C).

CITATION LIST

Patent Literature

Patent Literature 1: Japanese Patent Application Laid-Open No 2015-142646

Non-Patent Literature 1: a website (URL: http://www.metran.co.jp/products/products2/190.html) [date of retrieval: May 31, 2016] of Metran Co., Ltd., [online], Products>Jusmine

SUMMARY OF INVENTION

Technical Problem

However, in the conventional respiratory assistance devices and CPAP devices, a pressure and a flow rate are set on a hospital side, and a user cannot change the set values. Since whether the set values are appropriate or not depends on the user's daily physical condition, the user cannot help using the respiratory assistance device with it being hard to breathe in some cases.

Since the user cannot change settings to select a comfort pressure and a flow rate while the respiratory assistance device is being operated, the user can often experience difficulty in sleeping while actually using the device. There is a problem that the percentage of users who continuously use the CPAP drops to the order of 50% to 70% after one year from the start of using the respiratory assistance device.

The present invention has been made in view of the aforementioned problems, and has an object of providing a respiratory assistance device and the like that can make a setting for respiratory assistance modes and the like while a user is breathing with the respiratory assistance device being operated.

Solution to Problem

The present invention is a respiratory assistance device that is connected to a user's airway and regulates an airway pressure to assist ventilation. The respiratory assistance device has a plurality of different respiratory assistance modes. The respiratory assistance device includes a mode input reception unit configured to receive an input of a setting for the respiratory assistance mode during operation of an air blower that blows air into the user's airway, and an assistance level control unit configured to, when the mode input reception unit has received the input of the setting, control a flow rate or a pressure of air supplied from the air blower in reflection to the respiratory assistance mode in which the setting has been inputted, while the air blower is kept operating.

According to the above-described invention, while the user is breathing with the respiratory assistance device being operated, the respiratory assistance modes different from each other can be selected and set, and a selection result is immediately reflected in respiratory assistance. Therefore, the respiratory assistance device has the beneficial effect of facilitating selection of a flow rate setting and a pressure that feels comfortable to the user.

In relation to the above-described respiratory assistance device, at least one of the respiratory assistance modes is an undershoot mode in which a predetermined pressure decrease time is provided. In the pressure decrease time, the pressure is decreased from a set expiratory reference pressure of the airway pressure by a predetermined pressure decrease width in an expiratory period in which the user exhales a breath.

According to the above-described invention, while the user is breathing with the respiratory assistance device being operated, the pressure can be decreased from the set minimum pressure (prescribed pressure) by only the predetermined pressure especially in the expiratory period, in which the user exhales the breath, for the predetermined time to facilitate exhalation. Therefore, the respiratory assistance device has the beneficial effect of easily finding out an easy expiratory condition.

In relation to the above-described respiratory assistance device, the mode input reception unit can independently set the predetermined pressure decrease width and the predetermined pressure decrease time.

According to the above-described invention, when the pressure is decreased from the set minimum pressure (prescribed pressure) by the predetermined pressure for the predetermined time to facilitate exhalation while the user is breathing with the respiratory assistance device being operated, the pressure decrease time and the pressure decrease width can be independently regulated. Therefore, the respiratory assistance device has the outstanding effect of realizing the most comfortable respiratory assistance for each individual user.

The above-described respiratory assistance device has a plurality of the undershoot modes in which the predetermined pressure decrease widths or the predetermined pressure decrease times are different from each other.

In relation to the above-described respiratory assistance device, the predetermined pressure decrease time is within 10 seconds.

Since the time for which the pressure is decreased from the set minimum pressure (prescribed pressure) in the expiratory period is limited to within 10 seconds, the above-described invention has the effect of realizing respiratory assistance that facilitates breathing, with preventing clogging of the airway as much as possible, without elongating an apnea state.

In relation to the above-described respiratory assistance device, at least one of the respiratory assistance modes is an overshoot mode in which a pressure increase time is provided. In the pressure increase time, the pressure is increased from a set inspiratory reference pressure of the airway pressure by a predetermined pressure increase width in an inspiratory period in which the user inhales a breath.

According to the above-described invention, while the user is breathing with the respiratory assistance device being operated, the pressure can be further increased from the prescribed pressure (for example, the set maximum pressure) by only the predetermined pressure especially in the inspiratory period in which the user inhales the breath, to facilitate inhalation. Therefore, the respiratory assistance device has the beneficial effect of easily finding out an easy inspiratory condition.

In relation to the above-described respiratory assistance device, the mode input reception unit can independently set the predetermined pressure increase width and the predetermined pressure increase time.

According to the above-described invention, when the pressure is increased from the prescribed pressure (for example, set maximum pressure) by the predetermined pressure for the predetermined time to facilitate inhalation while the user is breathing with the respiratory assistance device being operated, the pressure increase time and the pressure increase width can be independently regulated. Therefore, the respiratory assistance device has the outstanding effect of realizing the most comfortable respiratory assistance for each individual user.

The above-described respiratory assistance device has a plurality of the overshoot modes in which the predetermined pressure increase widths or the predetermined pressure increase times are different from each other.

In relation to the above-described respiratory assistance device, the predetermined pressure increase time is within 10 seconds.

Since the time for which the pressure is increased from the set maximum pressure (prescribed pressure) in the inspiratory period is limited to within 10 seconds, the above-described invention has the effect of realizing respiratory assistance that facilitates breathing, without excessively pressing compressed air into the airway.

The respiratory assistance device includes a display configured to display a setting screen for setting the respiratory assistance mode.

Since the above-described invention can realize the function of displaying the setting screen for setting the respiratory assistance mode, a normal user who does not have medical knowledge, other than a doctor, a nurse or the like, can easily set the respiratory assistance mode while looking at the screen.

The above-described respiratory assistance device includes an assistance level input reception unit configured to receive an input of a setting for a prescribed inspiratory assistance level for a patient, and an assistance level set permission unit configured to request the user to perform a specific input operation before setting the assistance level, prior to operating the assistance level input reception unit, and to permit the operation of the assistance level input reception unit when the specific input operation satisfies a predetermined condition. On the other hand, the mode input reception unit eliminates a need to perform the specific input operation before input of a setting for the respiratory assistance mode.

According to the above-described invention, when the doctor manages the specific input operation, the assistance level input reception unit becomes a unit specific to the doctor. Since the patient cannot arbitrarily change a prescribed expiratory flow rate and the like, the respiratory assistance device has the effect of improving safety.

In relation to the above-described respiratory assistance device, the assistance level set permission unit and the assistance level input reception unit are operated during operation of the air blower that blows air into the user's airway. When the assistance level input reception unit has received the prescribed expiratory assistance level, the assistance level control unit controls an assistance level of air supplied from the air blower so as to reflect the prescribed expiratory assistance level while the air blower is kept operating.

According to the above-described invention, since an air flow can be changed to a desired assistance level during operation of the air blower that blows air into the user's airway, it is possible to appropriately regulate the assistance level in the user's actual sleep posture and breathing state. The above-described invention has the outstanding effect of realizing positive pressure ventilation that is effective and more comfortable for the user.

The present invention is a respiratory assistance device that is connected to a user's airway and regulates an airway pressure to assist ventilation. The respiratory assistance device includes an assistance level input reception unit configured to receive an input of a setting for a prescribed expiratory assistance level for a patient during operation of an air blower that blows air into the user's airway, and an assistance level control unit configured to, when the assistance level input reception unit has received the prescribed expiratory assistance level, control an assistance level of air supplied from the air blower in reflection to a result of the prescribed expiratory assistance level while the air blower is kept operating.

According to the above-described invention, the assistance level of air supplied from the air blower can be controlled in reflection to the result of the prescribed expiratory assistance level while the air blower is kept operating. Therefore, it is possible to appropriately regulate the assistance level in the user's actual sleep posture and breathing state. The above-described invention has the outstanding effect of realizing positive pressure ventilation that is effective and more comfortable for the user.

The present invention is a respiratory assistance program for controlling a respiratory assistance device that is connected to a user's airway and regulates an airway pressure to assist ventilation. The respiratory assistance program has a plurality of different respiratory assistance modes. The respiratory assistance program causes a computer of the respiratory assistance device to realize a mode input reception function that receives an input of a setting for the respiratory assistance mode during operation of an air blower that blows air into the user's airway, and an assistance level control function that, when the mode input reception function has received the input of setting, controls an assistance level of air supplied from the air blower in reflection to the respiratory assistance mode in which the setting has been inputted while the air blower is kept operating.

In relation to the above-described respiratory assistance program, at least one of the respiratory assistance modes is an undershoot mode in which a predetermined pressure decrease time is provided. In the pressure decrease time, the pressure is decreased from a set expiratory reference pressure of the airway pressure by a predetermined pressure decrease width in an expiratory period in which the user exhales a breath.

In relation to the above-described respiratory assistance program, at least one of the respiratory assistance modes is an overshoot mode in which a pressure increase time is provided. In the pressure increase time, the pressure is increased from a set inspiratory reference pressure of the airway pressure by a predetermined pressure increase width in an inspiratory period in which the user inhales a breath.

The above-described respiratory assistance program includes an assistance level input reception function that receives an input of a setting for a prescribed inspiratory assistance level for a patient, and an assistance level set permission function that requests the user to perform a specific input operation before setting the assistance level, prior to performing the assistance level input reception function, and permits the assistance level input reception function when the specific input operation satisfies a predetermined condition. On the other hand, before the mode input reception function is performed, the specific input operation is unnecessary.

In relation to the above-described respiratory assistance program, the assistance level set permission function and the assistance level input reception function are performed during operation of the air blower that blows air into the user's airway. When the assistance level input reception function has received the prescribed expiratory assistance level, the assistance level control function controls the assistance level of air supplied from the air blower so as to reflect the prescribed expiratory assistance level while the air blower is kept operating.

The present invention is a respiratory assistance program for controlling a respiratory assistance device that is connected to a user's airway and regulates an airway pressure to assist ventilation. The respiratory assistance program causes a computer to realize an assistance level input reception function that receives an input of a setting for a prescribed expiratory assistance level for a patient during operation of an air blower that blows air to the user's airway, and an assistance level control function that, when the assistance level input reception function has received the prescribed expiratory assistance level, controls an assistance level of air supplied from the air blower in reflection of a result of the prescribed expiratory assistance level while the air blower is kept operated.

Advantageous Effect of Invention

According to the respiratory assistance program and the respiratory assistance device described herein, while the user is breathing with the respiratory assistance device being operated, the respiratory assistance modes different from each other can be selected and set, and a selection result is immediately reflected in respiratory assistance. Therefore, the respiratory assistance program and device have the beneficial effect of facilitating selection of a flow rate setting and a pressure in which the user feels comfortable.

DESCRIPTION OF EMBODIMENTS

Figure 1A:
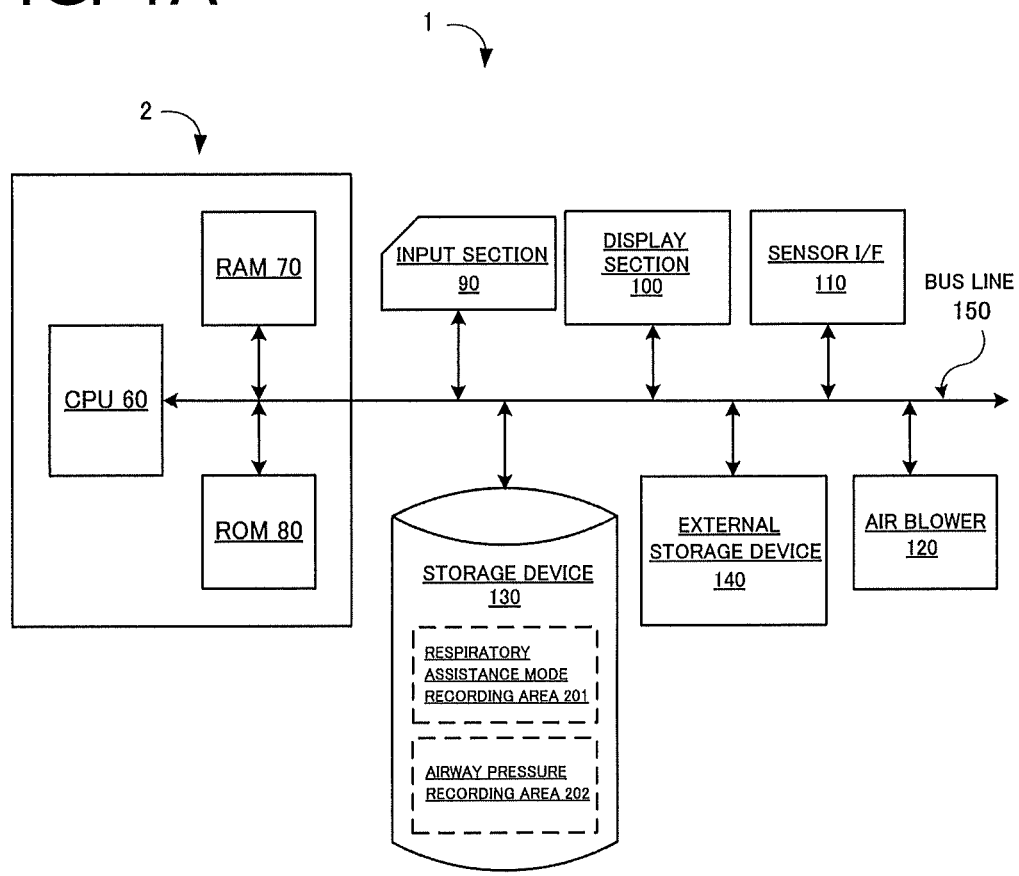
FIG. 1A is a block diagram of a control system in a respiratory assistance device according to a first embodiment of the present invention.

Embodiments of the present invention will be described below with reference to attached drawings.

FIGS. 1 to 5 show an example of an embodiment of the invention, and the same reference numerals indicate the same components in the drawings. In each of the drawings, a part of the configuration is appropriately omitted to simplify the drawing. The size, shape, thickness and the like of the components are approximately exaggerated.

FIG. 1A is a block diagram of a control system in a respiratory assistance device 1 according to a first embodiment of the present invention.

The respiratory assistance device 1 is connected to a user's airway and regulates an airway pressure to assist ventilation. The respiratory assistance device 1 has a plurality of different respiratory assistance modes. The respiratory assistance device 1 is characterized as including an input reception unit configured to receive an input of a setting for the respiratory assistance modes during operation of an air blower that blows air into the user's airway, and an assistance level control unit configured to control a flow rate or a pressure of air from the air blower in reflection of a result of the input of the setting when the input reception unit has received the input of the setting.

Figure 8:
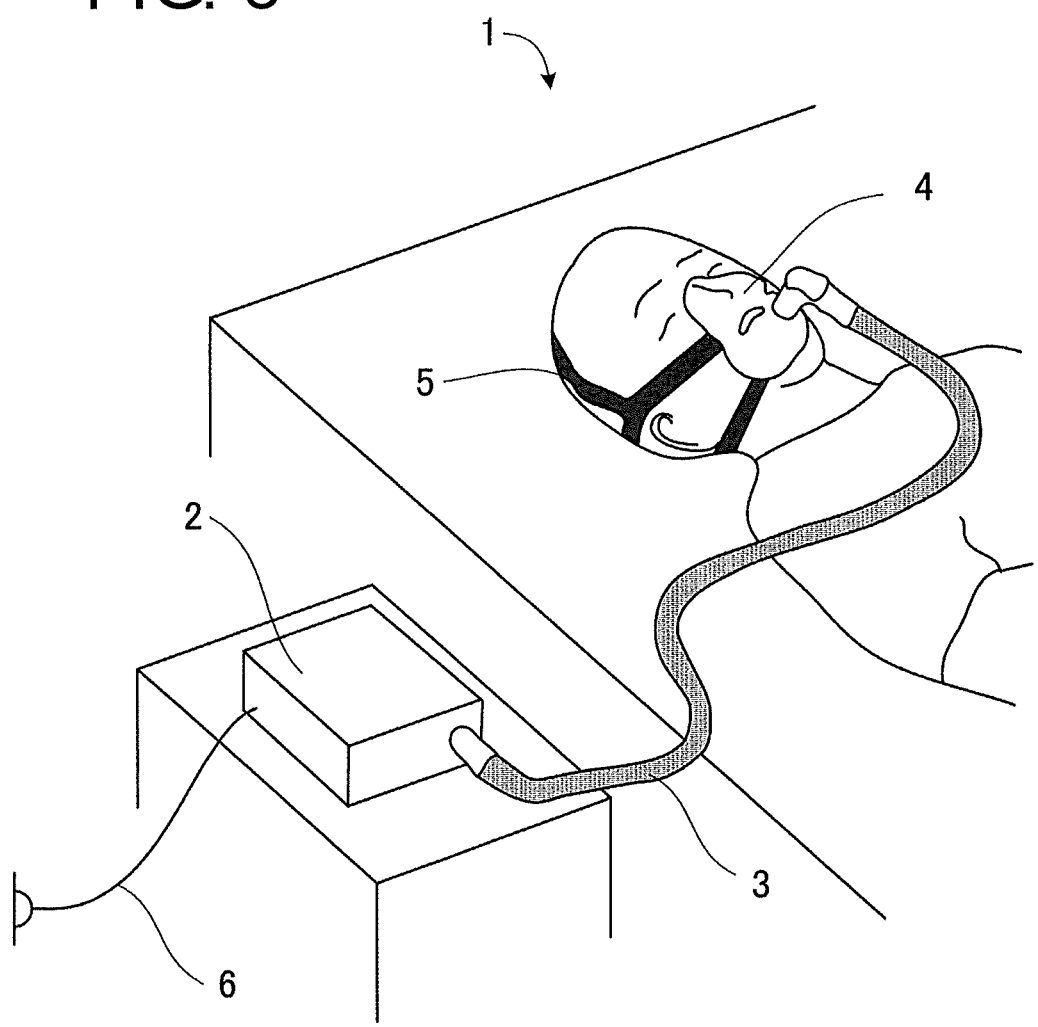
FIG. 8 is an explanatory view that explains usage of a conventional CPAP device.
Figure 9A:
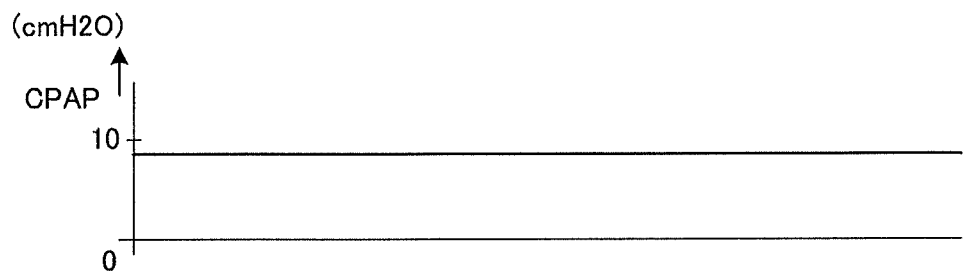
FIG. 9A is an explanatory view for explaining variation with time in pressure that a fixed pressure CPAP device applies to an airway.
Figure 9B:
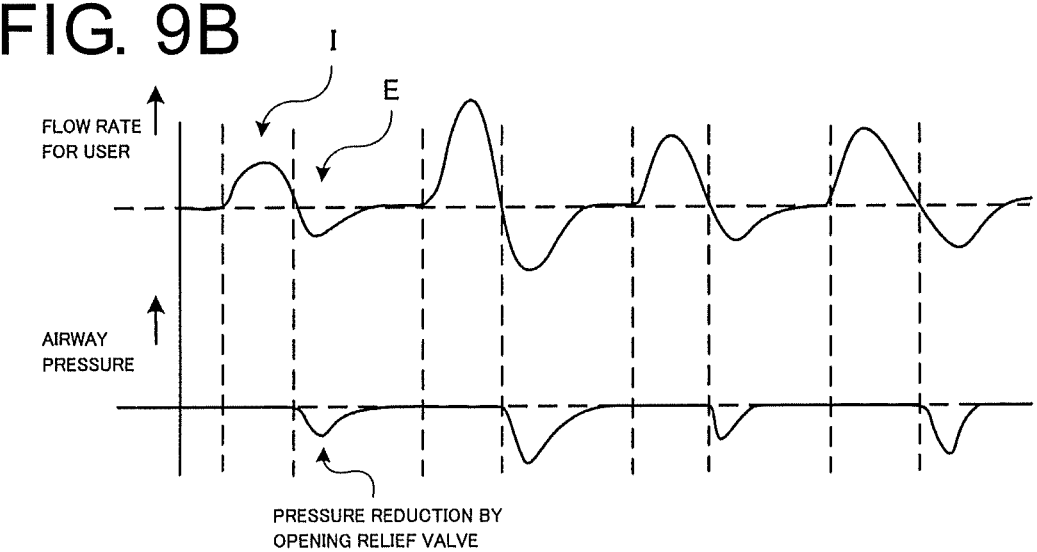
FIG. 9B is an explanatory view for explaining temporary reduction in a flow rate and pressure of compressed air supplied to a user by an Auto-CPAP device having a relief valve due to opening of the relief valve at the start of an expiratory period.
Figure 9C:
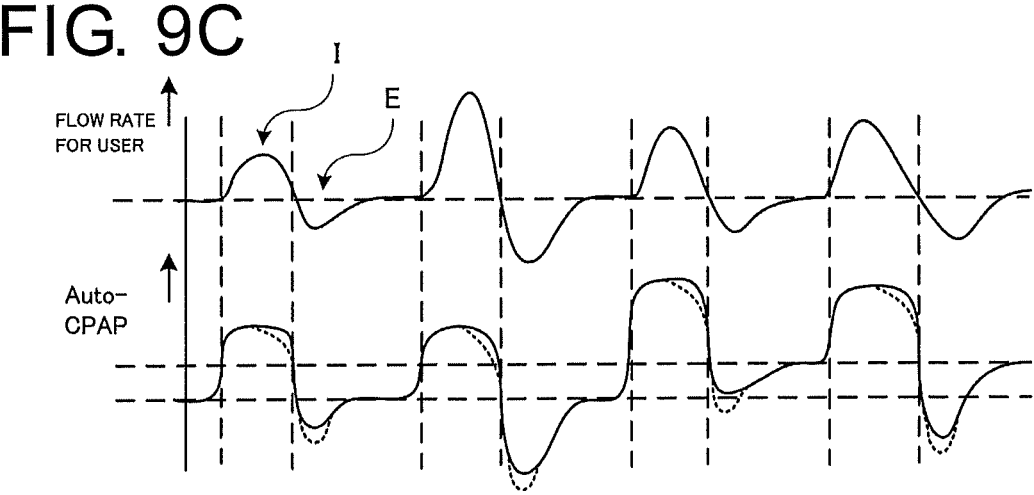
FIG. 9C is an explanatory view for explaining variation with time in the flow rate and pressure of the compressed air supplied by the Auto-CPAP to the user.

More specifically, the respiratory assistance device 1 is mainly constituted of a control unit 2, an input section 90 connected to a bus line 150 of the control unit 2, a display section 100, a sensor I/F 110, an air blower 120, a storage device 130, and a detachable external storage device 140. Besides, it is desired to include the same components as the conventional CPAP device shown in FIG. 8, i.e., the mounting section 4 that the user wears, the mounting section fixing tool 5, the air tube 3, a humidifier to humidify compressed air to be blown, and a relief valve for pressure reduction. The respiratory assistance device 1 may be supplied with power through an AC power line 6 or may be operated by a battery provided in the respiratory assistance device 1.

The control unit 2 is mainly constituted of a CPU 60, a RAM 70 and a ROM 80, and performs various types of control. The CPU, which is a so-called central processing unit, realizes various functions by execution of a respiratory assistance program and other various programs. The RAM is used as a working area and a storage area of the CPU, and the ROM stores an operating system, the respiratory assistance program and the like to be executed by the CPU.

The input section 90 may be a keyboard, a mechanical switch or a touch panel provided in the display section 100 described later.

The display section 100 is a liquid crystal display that displays various types of control information including a prescribed pressure and the like, a flow rate of compressed air to be blown, an airway pressure, a setting selection screen and the like.

The sensor I/F 110 is an input-output interface of a flow rate sensor that measures the flow rate of the compressed air and a pressure sensor that measures the airway pressure. The air blower 120 is a so-called blower that blows compressed air.

The storage device 130 is an electromagnetic recording unit such as a hard disk, and desirably includes at least a respiratory assistance mode recording area 201 to record a setting for each respiratory assistance mode described later and the like, and an airway pressure recording area 202 to record the airway pressure, the flow rate of the compressed air to be blown and the like during use of the respiratory assistance device 1. The storage device 130 may store the respiratory assistance program.

The external storage device 140 is a detachable nonvolatile storage device that is used for copying information recorded in the airway pressure recording area 202 of the storage device 130 and providing a doctor with the information. The external storage device 140 is desirably a recording medium such as an SD card or a USB memory. The external storage device 140 may record the prescribed pressures prescribed by doctors, i.e. a maximum pressure and a minimum pressure. Other communication units may be provided, so that required information may be obtained by downloading information such as the prescribed pressure from doctors.

The control unit 2 desirably includes a power control function, a humidity control function, a water level control function, a blower revolution number control function, a device temperature control function, an alarm function for issuing an alarm upon receiving an abnormal signal from a sensor and the like, in addition to the above.

Figure 1B:
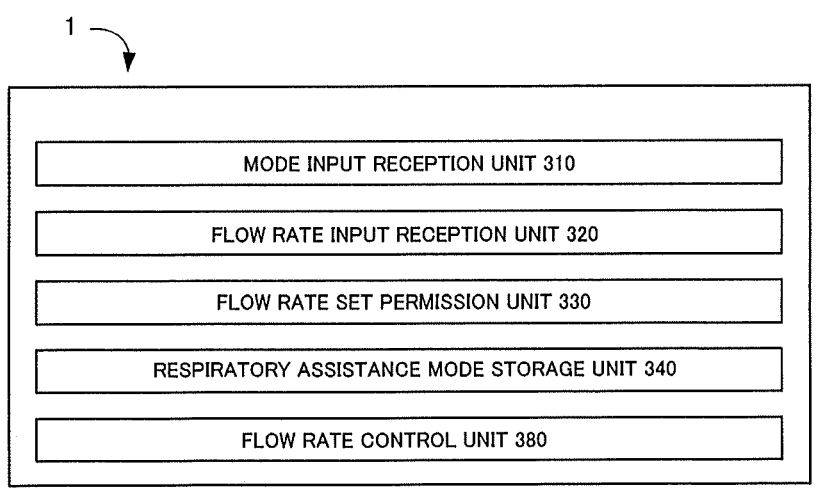
FIG. 1B is a diagram of functional blocks that are realized by a respiratory assistance program executed by the respiratory assistance device.
Figure 2:
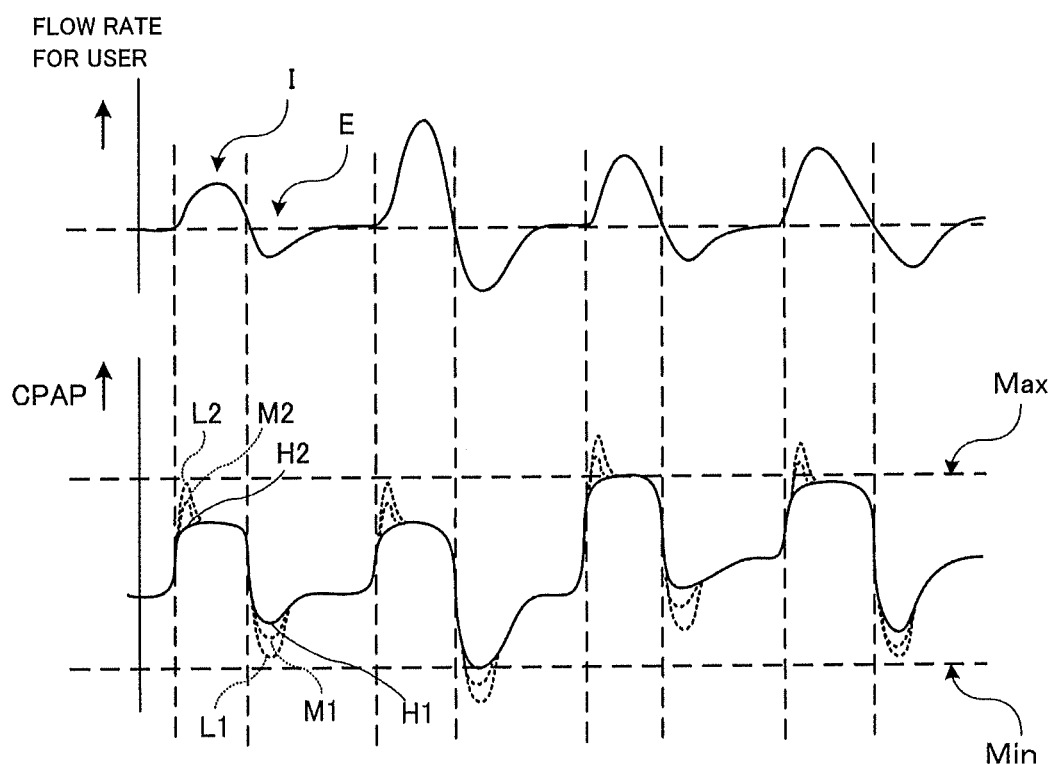
FIG. 2 is an explanatory view showing variation with time in a flow rate of compressed air, the feeding of which is controlled by the respiratory assistance program, and variation with time in pressure applied in accordance with CPAP treatment.

FIG. 1B is a block diagram that explains various types of units realized by the respiratory assistance device 1 by execution of the respiratory assistance program by the respiratory assistance device 1.

The respiratory assistance device 1 has a mode input reception unit 310, a flow rate control unit 380, a flow rate input reception unit 320, a flow rate set permission unit 330, and a respiratory assistance mode storage unit 340. Note that the flow rate control unit 380 configured to control an air flow rate is adopted here as an example of the assistance level control unit configured to control a respiratory assistance level, but the present invention is not limited thereto, and a pressure control unit configured to control an air pressure may be used instead. However, to control the air pressure (pressure inside an airway), the air flow rate is required to be controlled after all. Therefore, since a pressure and a flow rate are the same kind of concepts as assistance levels, and the flow rate control unit and the pressure control unit are collectively referred to as the assistance level control unit in the present invention.

The respiratory assistance mode storage unit 340 stores an execution program to realize a plurality of different respiratory assistance modes. In the first embodiment, there are provided an undershoot mode and an overshoot mode as the respiratory assistance modes. In the undershoot mode, a pressure is decreased from a set expiratory reference pressure (e.g., a set minimum pressure) of the airway pressure by a predetermined pressure decrease width (pressure decrease amount) and is held for a predetermined time in an expiratory period in which the user exhales a breath. In the overshoot mode, a pressure increase time in which the pressure is increased from a set inspiratory reference pressure (e.g., a set maximum pressure) of the airway pressure by a predetermined pressure increase width is provided in an inspiratory period in which the user inhales a breath.

Furthermore, the respiratory assistance mode storage unit 340 preferably has a plurality of undershoot modes, as the undershoot mode, in which the pressure decrease widths or the pressure decrease times are different from each other (for example, two levels including level 1 and level 2). In the same manner, the respiratory assistance mode storage unit 340 preferably has a plurality of overshoot modes, as the overshoot mode, in which the pressure increase widths or the pressure increase times are different from each other (for example, two levels including level 1 and level 2). The pressure decrease time of the undershoot mode and the pressure increase time of the overshoot mode are each preferably set to be 10 seconds or less.

The mode input reception unit 310 receives an input of a setting for the respiratory assistance mode from the user during operation of the blower (during operation of the air blower 120) that blows air into the user's airway with the use of the input section 90. At this time, the plurality of respiratory assistance modes (for example, overshoot modes (OFF, level 1, and level 2) and undershoot modes (OFF, level 1, and level 2)), which are stored in the respiratory assistance mode storage unit 340, may be displayed in the display section 100 to allow the user to select a desired respiratory assistance mode among them. To be more specific, in the undershoot mode, the setting for the pressure decrease width and the pressure decrease time may be independently input. Instead of inputting the desired numeric values, the pressure decrease width and the pressure decrease time may be independently selected from a plurality of pressure decrease widths and a plurality types of pressure decrease times. In the same manner, in the overshoot mode, setting for the pressure increase width and the pressure increase time may be independently input. Instead of inputting the desired numeric values, the pressure increase width and the pressure increase time may be independently selected from a plurality of pressure increase widths and a plurality types of pressure increase times.

The flow rate input reception unit 320 receives an input of a setting for a prescribed expiratory flow rate for a patient (user) (this may be a pressure input reception unit, and collectively referred to as an assistance level input reception unit). Since this type of respiratory assistance device 1 is generally provided for the patient as medical equipment on the basis of a prescription of the doctor, the doctor determines the prescribed flow rate by the patient's diagnosis.

Before operating the flow rate input reception unit 320 (in other words, before entering a state of receiving an input of a setting), the flow rate set permission unit 330 requests the user to perform a specific input operation before setting a flow rate. When the specific input operation satisfies a predetermined condition, the operation of the flow rate set permission unit 330 is permitted. In other words, the flow rate set permission unit 330 provides a locking function of the flow rate input reception unit 320. The specific input operation is preferably, for example, an input of specific information including a password and the like, a specific operation such as a press of a plurality of buttons at the same time, in a predetermined sequence or for a predetermined time, or a specific operation such as an approach, a contact or an insertion of an external key serving as a release key (including an IC chip, an external memory, a USB or the like limited to an actual key) to, with or into the respiratory assistance device 1. By these operations, the doctor manages the specific input operations, so that the flow rate input reception unit 320 becomes a doctor-specific operation unit. The patient therefore cannot arbitrarily change the prescribed expiratory flow rate, thus improving safety. The prescribed flow rate or the prescribed pressure may be set through the external storage device 140, instead of being inputted from the input section 90.

Although it is not especially described herein, the flow rate set permission unit 330 can shift from a lock release state to a lock state by reception of the specific input operation from the doctor. In other words, the same or different specific input operation may be received in both of transition to the lock state and transition to the lock release state. As a matter of course, when a predetermined time has elapsed from release of a lock state, the flow rate set permission unit 330 may automatically transit to the lock state.

On the other hand, the mode input reception unit 310 does not require this kind of specific input operation, and the patient can make setting thereon anytime. This is because a mode change does not change the prescribed flow rate.

The mode input reception unit 310, the flow rate input reception unit 320, and the flow rate set permission unit 330 function even during operation of the air blower 120. In other words, these components can be operated during operation. Therefore, by a mode change, the user can regulate the assistance levels, for example, the pressure and the flow rate, though in a temporary manner, without any specific input operation. In other words, the respiratory assistance device 1 that is connected to a user's airway and regulates an airway pressure to assist ventilation is characterized as including a prescribed assistance level setting unit capable of changing a setting for a prescribed assistance level when a predetermined specific input operation is performed, and also including an assistance level change reception unit capable of allowing the user to temporarily change the setting by a predetermined assistance level from the prescribed assistance level even when the specific input operation is not performed. Therefore, it is possible to select an optimal mode in accordance with the user's posture during actual use, for example, in a lying state on a bed, and more specifically to select a weak setting in the overshoot mode, and to select a strong setting in the undershoot mode. This provides the excellent effect of enabling comfortable sleep for the user.

When the mode input reception unit 310 has received an input of a setting, the flow rate control unit 380 controls a flow rate of air supplied from the air blower 120 in reflection to (by changing to) a respiratory assistance mode in which the setting has been inputted, while the air blower 120 is kept operating. In the same manner, when the flow rate input reception unit 320 has received a new prescribed expiratory flow rate, the flow rate control unit 380 controls a flow rate of air supplied from the air blower 120 so as to reflect the prescribed expiratory flow rate while the air blower 120 is kept operating. To control the flow rate, the number of revolutions of the air blower 120 or the like may be directly controlled, or a flow rate control valve or the like disposed downstream may be controlled instead. To check whether or not the flow rate is correctly controlled, the respiratory assistance device 1 is preferably provided with a flowmeter.

A method in which the flow rate control unit 380 controls the air flow to the user with the use of the prescribed flow rate as the prescribed assistance level, but a prescribed pressure may be used as the prescribed assistance level. To control the pressure of the air flow, a buffer tank may be provided in the middle of a flow path of the air flow, and the pressure may be always measured and controlled using a pressure regulating valve.

Next, the operation of the respiratory assistance device 1 will be described.

When a user who is suspected of having sleep apnea syndrome visits a doctor, the doctor admits the user to a hospital for overnight inspection in a state in which the user wears the operated respiratory assistance device 1 and measures the effects on breathing, pulses, blood pressure and the like using a polygraph, which records a breathing state during sleep, to determine a proper pressure for each user. Determined prescribed pressures, i.e. a maximum pressure and a minimum pressure, are set on the control unit 2.

Also in this case, since the respiratory assistance device 1 is unlocked by the flow rate set permission unit 330 during operation of the air blower 120, to enable a change of a flow rate in real time using the flow rate input reception unit 320, it is possible for the doctor to verify an optimal prescribed expiratory flow rate by observing a state of the patient while changing the flow rate.

When the prescribed expiratory flow rate is determined, the flow rate set permission unit 330 performs a locks operation in order to prevent the user from changing the prescribed pressures (prescribed assistance levels).

Upon setting the prescribed pressures, the respiratory assistance device 1 controls a flow rate of air from the air blower 120 under control of the control unit 2. The control unit 2 simultaneously records a breathing state of the user. In other words, information from a flowmeter (not illustrated) and a pressure sensor (not illustrated) connected to the sensor I/F 110 is recorded to the airway pressure recording area 202 of the storage device 130. In order for the doctor to check the effects of treatment, the information recorded to the airway pressure recording area 202 may be appropriately copied to the external storage device 140. During operation of the respiratory assistance device 1, a flow rate, a pressure of an airway and the like may be displayed on the display section 100.

The user who has received the respiratory assistance device 1 wears the mounting section 4 of the respiratory assistance device 1 on his or her nose or mouth at his/her home or the like, turns the power on, and operates the air blower 120, to check whether or not he or she breathes comfortably. At this time, respiratory assistance modes are changed through a respiratory assistance program. A concrete process will be described later with reference to a flowchart.

The respiratory assistance modes are first described in detail. When the user selects an Auto mode in the respiratory assistance device 1, a flow rate of compressed air blown from the air blower 120 varies with time in accordance with breathing detected by the pressure sensor (not illustrated) in Inhalation (inspiratory) periods I and Exhalation (expiratory) periods E shown in an upper graph of FIG. 2. At this time, an airway pressure also varies with time as indicated by a solid line in a lower graph of FIG. 2, but is kept between a minimum pressure Min and a maximum pressure Max, i.e. prescribed pressures, inclusive in principle in order to prevent clogging of the airway.

In the first half of the Inhalation (inspiratory) period I, an increase in pressure in the direction of pushing air into the airway facilitates breathing. Accordingly, as a respiratory assistance mode, an overshoot (OS) mode (function) in which a pressure increase time to increase the pressure from the set maximum pressure Max (reference inspiratory pressure) of the airway pressure by a predetermined pressure increase width is provided in the inspiratory period in which the user inhales a breath. For example, a small overshoot pressure M2 (level 1) or a large overshoot pressure L2 (level 2) can be selected. If no overshoot is comfortable for the user, a no overshoot pressure H2 (OFF) mode can be selected.

As to each of M2 and L2, the predetermined pressure increase width and the predetermined pressure increase time can be independently regulated. To properly realize the prescribed pressures, the predetermined pressure increase time may be limited to within 10 seconds.

In the first half of the Exhalation (expiratory) period E, a decrease in pressure in the direction of exhaling air from the airway facilitates breathing. Accordingly, as a respiratory assistance mode, an undershoot (US) mode (function) in which a pressure decrease time to decrease the pressure from the set minimum pressure (reference expiratory pressure) of the airway pressure by a predetermined pressure decrease width is provided in the expiratory period in which the user exhales a breath. For example, a small undershoot pressure M1 (level 1) or a large undershoot pressure L1 (level 2) can be selected. If no undershoot is comfortable for the user, a no undershoot pressure H1 (OFF) mode can be selected.

As to each of M1 and L1, an additional function capable of independently regulating the predetermined pressure decrease width and the predetermined pressure decrease time is provided. To properly realize the prescribed pressures, the predetermined pressure decrease time may be limited to within 10 seconds.

Therefore, while the user breathes with operation of the respiratory assistance device 1, the user selects and sets from the plurality of different respiratory assistance modes, and the selection result is immediately reflected in respiratory assistance. As a result, since the user can feel the difference between the respiratory assistance modes in real time before and after a change in the setting, the user can easily select a comfortable mode. Since the sense of the user such as ease of breathing is fuzzy, it is difficult, in actual fact, to grasp the difference between the modes, even if the air blower 120 of the respiratory assistance device 1 is once stopped and put in a different respiratory assistance mode and restarted.

Note that for the purpose of preventing a wrong mode change in a case where the user is a child or the like, a simple lock function in which a function selection screen is not displayed in the display section 100 may be provided to prevent a change of the overshoot (OS) setting and undershoot (US) setting. In this case, a safety management function is preferably provided such that a predetermined password is required to be input to change a mode, as usual. However, the operation of the simple lock function is different from that of the flow rate set permission unit 330.

Figure 4:
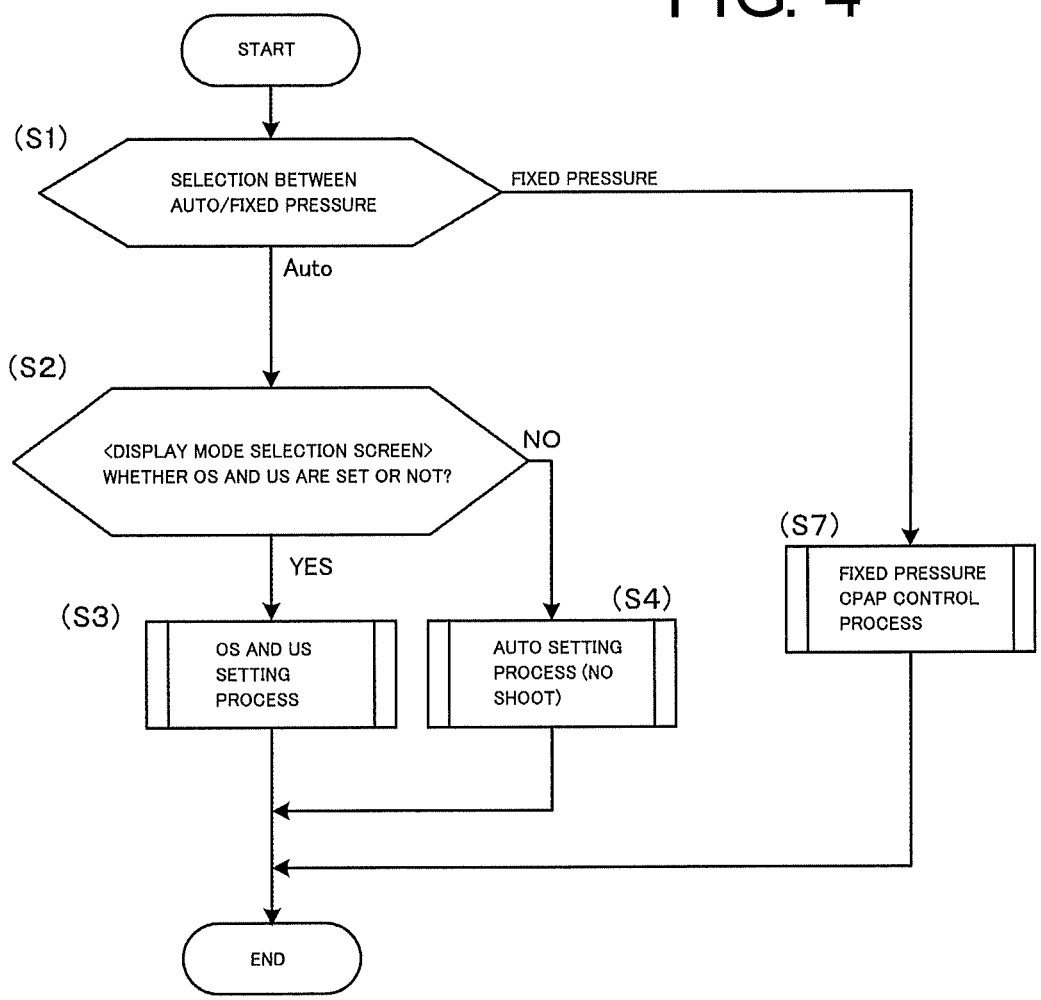
FIG. 4 is a main flowchart of a mode change process of the respiratory assistance program.
Figure 5:
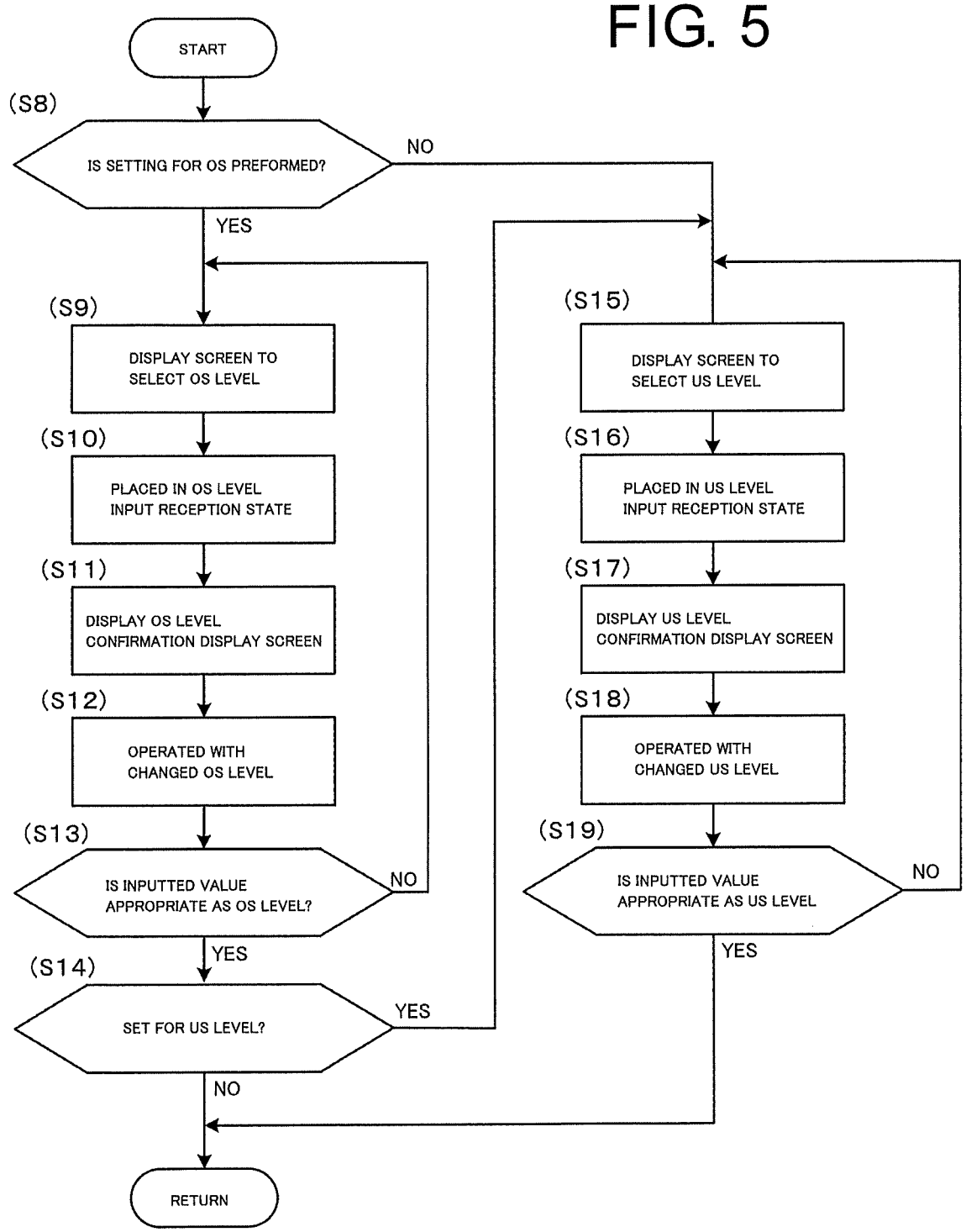
FIG. 5 is a flowchart that explains subroutines for realizing an overshoot function (mode) and an undershoot function (mode) of the mode change process.

Next, a process flow realized by the respiratory assistance program of the respiratory assistance device 1 will be described with reference to FIGS. 3 to 5.

Figure 3:
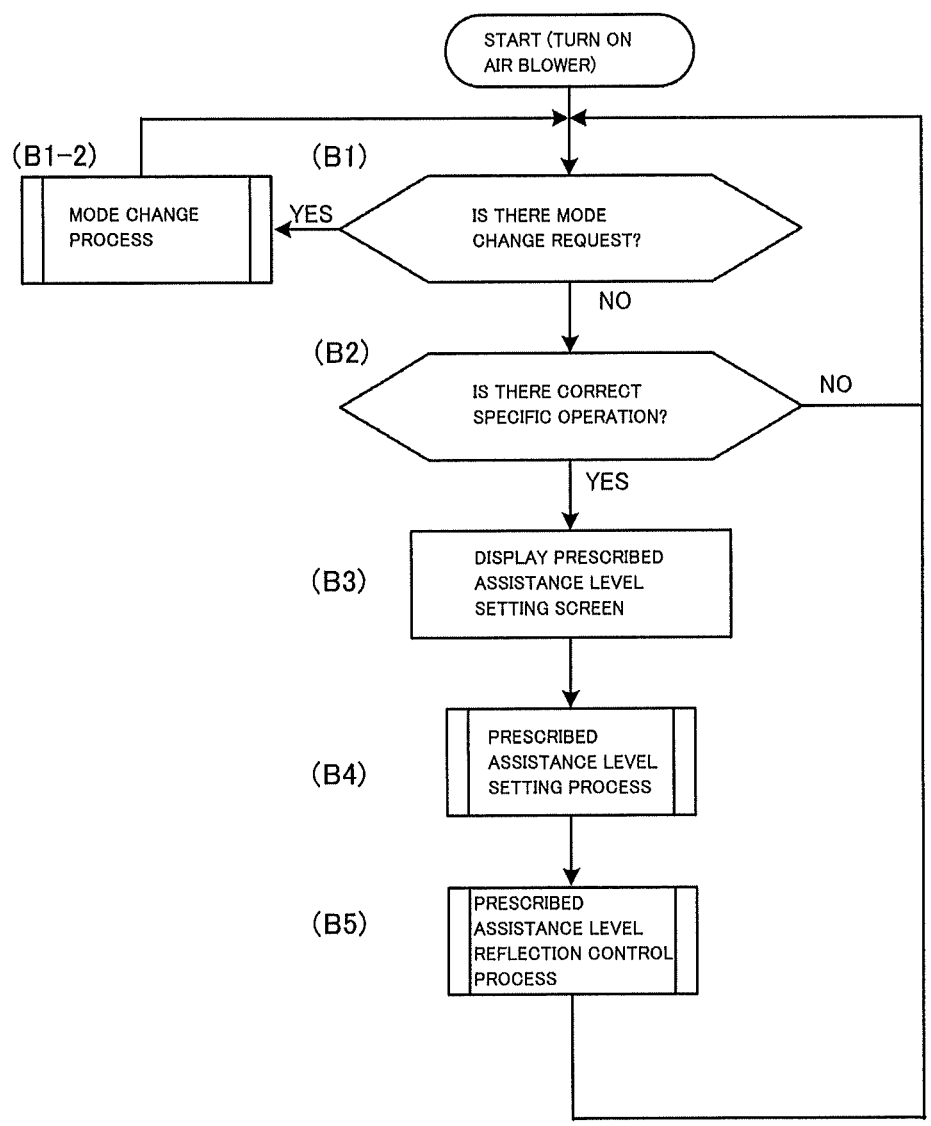
FIG. 3 is a basic flowchart of the respiratory assistance program.

FIG. 3 is a basic flowchart of the respiratory assistance program. First, upon turning on the respiratory assistance device 1, the air blower 120 is operated to start respiratory assistance. Although not especially illustrated, upon turning on the respiratory assistance device 1, the setting values (a prescribed assistance level and a respiratory assistance mode) that have been set immediately before turning off the device are automatically reflected as an operation mode.

After that, whether or not there is a request from a patient or the like to transit to a mode setting screen, in other words, the presence or absence of operation of a not-illustrated mode change button is checked (step B1). When a mode change request is present (if YES), the process proceeds to step B1-2, i.e., a mode change process. The mode change process will be described later in FIG. 4 or later. On the other hand, when the mode change request is absent (if NO), the process proceeds to step B2 to determine whether or not the flow rate set permission unit 330 receives a correct specific input operation from a doctor who knows a release method is judged. When the correct specific input operation is absent (if NO), the process returns to the beginning (step B1). On the other hand, when the correct specific input operation is present (if YES), the process proceeds to step B3 in which the flow rate input reception unit 320 receives an input of a prescribed flow rate or a prescribed pressure (prescribed assistance level) from the doctor. Upon receiving the input of the new prescribed assistance level, the process proceeds to step B4. While the air blower 120 is kept operating, the flow rate control unit 380 reflects the new prescribed assistance level by changing the number of revolutions of the air blower 120 or the like (step B5), and the process returns to the beginning.

Next, the "mode change process" in step B1-2 of the basic flowchart will be described with reference to a main flowchart of FIG. 4.

When the mode change process is started, the mode input reception unit 310 is actuated and placed in an input reception state in which an input of a setting for a respiratory assistance mode is received.

As operation categories of the respiratory assistance device, there are "fixed pressure CPAP operation" and so-called "Auto-CPAP operation" in which variation in pressure inside the mounting section 4 (refer to FIG. 8) due to a user's breathing is detected and compressed air is blown at a flow rate in accordance with inhalation and exhalation. A selection screen is displayed on the display section 100 to allow the user to select one of the operations (step S1). When the fixed pressure CPAP operation is selected in step S1, the fixed CPAP operation is performed at a constant prescribed pressure applied to an airway (step S7). This main flowchart is ended, and the process returns to the basic flowchart of FIG. 3.

On the other hand, when the Auto-CPAP operation is selected in step S1, the mode input reception unit 310 further displays the mode selection screen on the display section 100 (step S2). In the mode selection screen, the user is urged to select one of a normal Auto-CPAP operation (overshoot and undershoot are OFF) and an Auto-CPAP operation having an overshoot (OS) function and an undershoot (US) function. When the user selects a setting for OS and US (if YES), the process enters an OS and US setting process subroutine (step S3). Details on the subroutine will be described later with reference to FIG. 5. On the other hand, when the user does not select the setting for OS and US (if NO), the normal Auto-CPAP operation is performed (step S4), and the process returns to the basic flowchart of FIG. 3.

Next, the OS and US setting process subroutine in a "mode change process" of step S3 will be described in detail with reference to FIG. 5. In the subroutine, the mode input reception unit 310 displays a selection screen on the display section 100 to determine whether or not to perform a setting for OS (step S8). When the user selects to perform s setting for OS (if YES), the mode input reception unit 310 displays a screen to select an OS level (step S9). The OS level described here means the size of a predetermined pressure increase width by which the airway pressure is increased from a set maximum pressure, and a pressure increase time for which the pressure is increased. Note that a pressure increase speed at which the pressure is increased by the predetermined pressure increase width, or the like may be selected instead. Subsequently, the mode input reception unit 310 shifts to a state of receiving an input of the OS level, and waits for the input of a setting by the user (step S10).

When the input is accepted, the mode input reception unit 310 displays an OS level confirmation display screen as final confirmation (step S11). Upon finishing the confirmation, the flow rate control unit 380 performs an operation with the changed OS level (step S12). At this time, the respiratory assistance device 1 is characterized as changing its operation while continuing operation. In other words, while the user is breathing with the use of the respiratory assistance device 1 in an operated state, the pressure can be further increased from the set maximum pressure by only the predetermined pressure for a predetermined time in the inspiratory period in which the user inhales a breath in order to facilitate inhalation. Therefore, the respiratory assistance device 1 has the beneficial effect of easily finding out an easy inspiratory condition. At last, the flow rate control unit 380 displays a screen to select whether or not the input set value of the OS level is appropriate (step S13). When the user inputs that the OS value is appropriate, a setting screen to select whether or not a setting for a US level is to be further performed is subsequently displayed (step S14). If a setting for the US level is not performed, the subroutine is ended and the process returns to the main flowchart, and as a result, returns to the basic flowchart of FIG. 3. When the user inputs that the OS level is inappropriate in step S13, the program returns to the screen to select the OS level (step S9).

When the user selects to not set the OS level but provide a setting for the US level in the selection screen that selects whether or not a setting for the OS level is performed (if NO in step S8), or when the user inputs that a setting for the US level is to be further performed in step S14 (if YES), the mode input reception unit 310 displays a screen to select the US level (step S15). The US level used herein means the size of a predetermined pressure decrease width by which the airway pressure is decreased from a set minimum pressure and a pressure decrease time for which the pressure is decreased. Note that a pressure decrease speed at which the pressure is decreased by the predetermined pressure decrease width, or the like, may be selected instead. Subsequently, the program shifts to a state of receiving an input of the US level, and waits for an input of a setting by the user (step S16).

When the input is accepted, a US level confirmation display screen is displayed as a final confirmation (step S17). The flow rate control unit 380 performs an operation with the US level changed (step S18). At this time, the respiratory assistance device 1 is characterized as changing its operation while continuing operation. In other words, while the user is breathing with the use of the respiratory assistance device 1 in an operated state, the pressure can be further decreased from the set minimum pressure by only the predetermined pressure for a predetermined time in the expiratory period in which the user exhales a breath in order to facilitate exhalation. Therefore, the respiratory assistance device 1 has the beneficial effect of easily finding out an easy expiratory condition. At last, the mode input reception unit 310 displays a screen to select whether or not the input set value of the US level is appropriate (step S19). When the user inputs that the US value is appropriate (if YES), the subroutine is ended and the process returns to the main flowchart, and as a result, returns to the basic flowchart of FIG. 3. When the user inputs that the US level is inappropriate (if NO), the mode input reception unit 310 returns to the screen to select the US level (step S15).

In an aspect in which the flow rate of the air blower 120 is controlled in reflection of results of inputs of the settings for the OS and US levels, the control is realized by controlling the number of revolutions of the air blower 120, regulating the degree of opening of a valve (not illustrated) provided between the air blower and the air tube 3, regulating the degree of opening of a relief valve (not illustrated) provided in the vicinity of the mounting section 4, or the like.

FIG. 6 shows a key arrangement of the input section 90 of the respiratory assistance device 1, and mode setting screens displayed on the display section 100 by the respiratory assistance program.

Figure 6A:
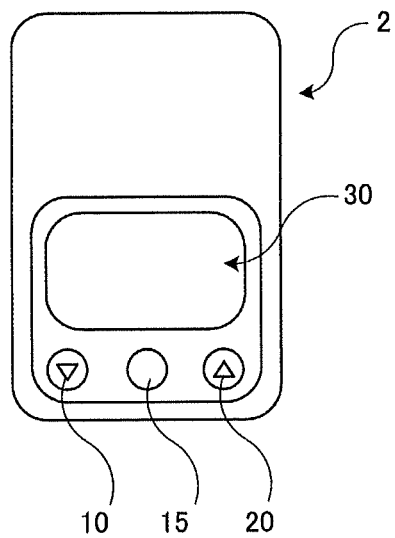
FIG. 6 includes explanatory views of a key arrangement provided to the respiratory assistance device and mode setting screens displayed by the respiratory assistance program.

FIG. 6A is a front view of the respiratory assistance device 1. The respiratory assistance device 1 is provided with a display screen 30 as the display section 100, and a Down key 10, an Up key 20 and a Menu/Enter key 15 as the input section 90. The display screen 30 may display various types of control information such as a prescribed pressure, a flow rate of compressed air to be blown, an airway pressure, a setting selection screen and the like. Variations in the flow rate of blown compressed air and the airway pressure with time may be graphed and displayed in the display screen 30 in real time.

Figure 6B:
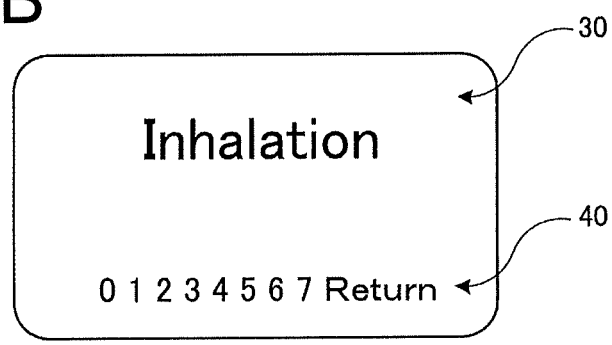

FIG. 6B is a setting screen to perform a setting in the Inhalation (inspiratory) period I. Even while the setting is performed, the respiratory assistance device 1 is kept operating. In an overshoot (OS) value selection screen 40, selection of an OS level is accepted. More specifically, a number of zero indicates an OS level of zero. The higher the number, the larger the pressure increase width becomes. A blink of each number indicates a state that the number is selectable. The user selects an OS level that the user himself or herself regards as appropriate with the use of the Down key 10 and the Up key 20, and determines the selection with the Menu/Enter key 15. After the user operates the Down key 10 and the Up key 20 until "Return" blinks, the setting is determined at the time when the input of the Menu/Enter key 15 is accepted. Immediately after the determination, operation is performed with the OS level changed, so that the user can judge whether or not the setting is appropriate.

Figure 6C:
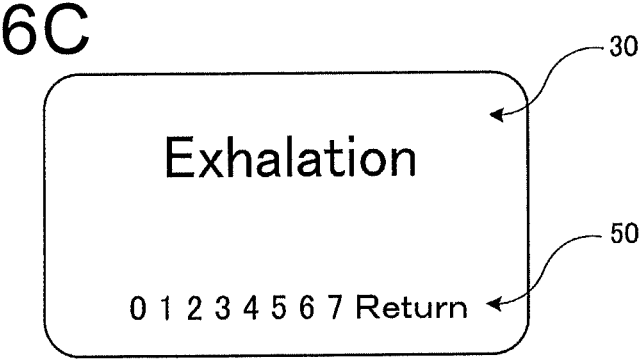

FIG. 6C is a setting screen to perform a setting in the Exhalation (expiratory) period E. Even while the setting is performed, the respiratory assistance device 1 is kept operating. In an undershoot (US) value selection screen 50, selection of a US level is accepted. More specifically, a number of zero indicates a US level of zero. The higher the number, the larger the pressure decrease width becomes. A blink of each number indicates a state that the number is selectable. The user selects a US level that the user himself or herself regards as appropriate with the use of the Down key 10 and the Up key 20, and determines the selection with the Menu/Enter key 15. After the user operates the Down key 10 and the Up key 20 until "Return" blinks, the setting is determined at the time when the input of the Menu/Enter key 15 is accepted. Immediately after the determination, operation is performed with the US level changed, so that the user can judge whether or not the setting is appropriate.

As to the OS level and the US level, initial values that the doctor regards to be appropriate may be set in advance. The set values may be recorded to the external storage device 140 and provided for the user. In the case of a child or a user who has a special disease, it is desirable that a safety management function is provided such that, for example, a predetermined password is required to be inputted to change a mode, in order to prevent the user from changing the setting for OS and US.

The control unit 2 may be wired to or wirelessly connected to the remaining portion of the respiratory assistance device 1, and remotely control the remaining portion. The control unit 2 may perform control functions as shown in FIG. 6 through an application of a portable communication terminal, i.e., a so-called smartphone. Particularly, the user can use the respiratory assistance device 1 while lying on a bed or the like at the time of sleep, thereby enabling the user to set and regulate the setting mode of the respiratory assistance device 1 in the lying posture, which has large effects on appropriate airway pressure and comfortable treatment.

As described above, the respiratory assistance device 1 according to the first embodiment can select and set the respiratory assistance modes different from each other and immediately reflect a selection result in respiratory assistance while the user is breathing with operation of the respiratory assistance device 1. Therefore, the respiratory assistance device 1 has the excellent effect of facilitating selection of a flow rate setting and a pressure that the user feels comfortable.

Figure 7:
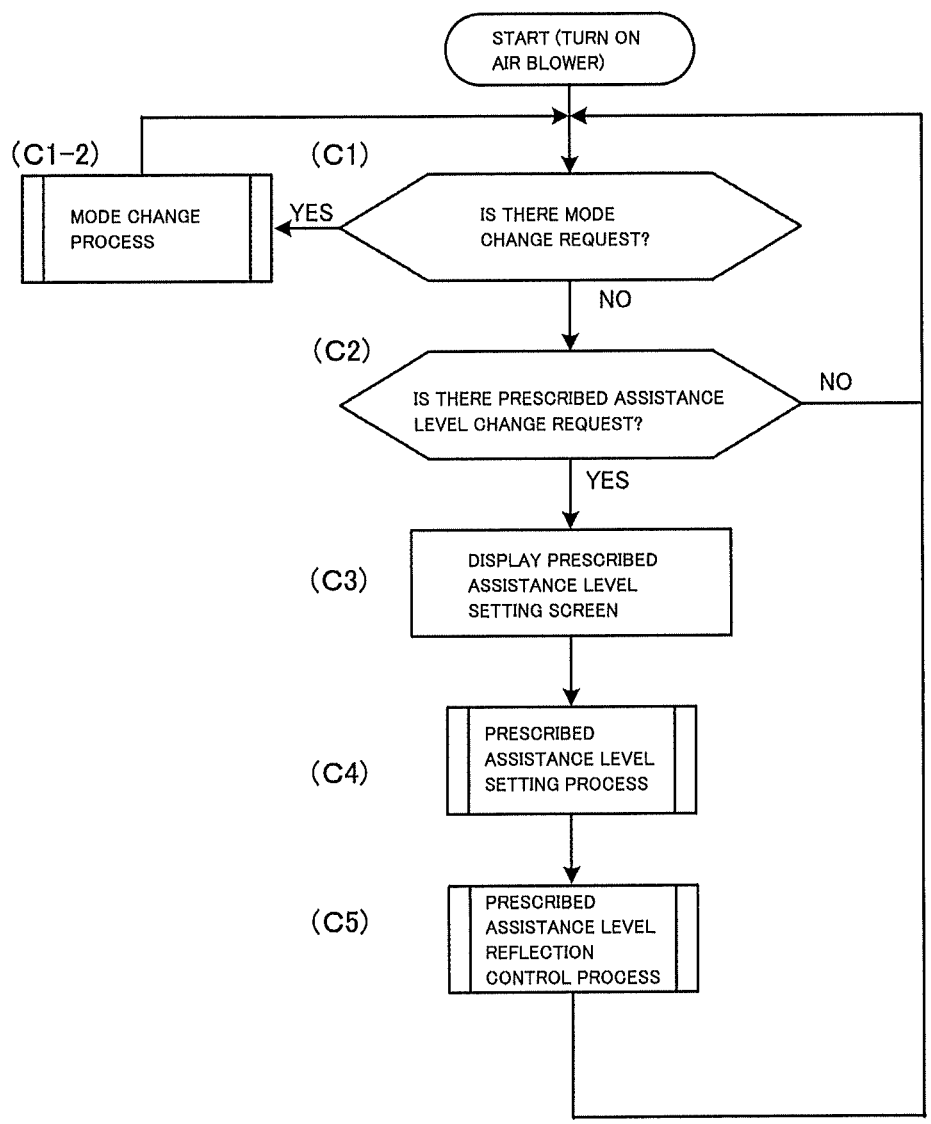
FIG. 7 is a basic flowchart including the function of requesting a change of a prescribed assistance level itself in a respiratory assistance device according to a second embodiment of the present invention.

FIG. 7 is a basic flowchart including the function of requesting a change of a prescribed assistance level itself in a respiratory assistance device according to a second embodiment of the present invention.

First, when the respiratory assistance device 1 is powered on, the air blower 120 is operated to start respiratory assistance. Although not especially illustrated, upon turning on the respiratory assistance device 1, the setting values (a prescribed assistance level and a respiratory assistance mode) that have been set immediately before turning off the device are automatically reflected as an operation mode.

After that, the presence or absence of a prescribed assistance level change request from a patient or the like, i.e., the presence or absence of the operation of a not-illustrated mode change button is checked (step C1). When a mode change request is present (if YES), the process shifts to step C1-2, i.e., a mode change process. The mode change process is the same as that described above with reference to FIG. 4 and the like. On the other hand, when the mode change request is absent (if NO), the process proceeds to step C2 to determine whether or not the prescribed assistance level change request is received. When the request is absent (if NO), the operation returns to the beginning (step C1). On the other hand, when the prescribed assistance level change request is present (if YES), the process proceeds to step C3 in which the flow rate input reception unit 320 receives an input of a prescribed flow rate or a prescribed pressure (prescribed assistance level) from a doctor. Upon receiving the input of a new prescribed assistance level, the process proceeds to step C4. While the air blower 120 is kept operating, the flow rate control unit 380 reflects the new prescribed assistance level by changing the number of revolutions of the air blower 120 or the like (step C5), and the process returns to the beginning.

Note that the respiratory assistance program and the respiratory assistance device of the present invention are not limited to the above-described embodiments, but, as a matter of course, can be variously modified within the scope not departing from the gist of the present invention.

REFERENCE SIGNS LIST 1 respiratory assistance device
2 control unit
3 air tube
4 mounting section
5 mounting section fixing tool
6 AC power line
10 Down key
15 Menu/Enter key 20 Up key
30 display screen
40 overshoot (OS) value selection screen
50 undershoot (US) value selection screen
60 CPU
70 RAM
80 ROM
90 input section
100 display section
110 sensor I/F
120 air blower
130 storage device
140 external storage device
150 bus line
201 respiratory assistance mode recording area
202 airway pressure recording area
I Inhalation (inspiratory) period I
E Exhalation (expiratory) period E
H1 no undershoot pressure
M1 small undershoot pressure
L1 large undershoot pressure
H2 no overshoot pressure
M2 small overshoot pressure
L2 large overshoot pressure

The invention claimed is:

1. A respiratory assistance device used during sleep as a continuous positive airway pressure therapy for a patient with sleep apnea syndrome, the respiratory assistance device being configured to be connected to a patient's airway and regulate an airway pressure to assist ventilation, the respiratory assistance device comprising:
   an air blower;
   a control unit which controls a flow rate of air from the air blower; and
   an input section;
   the respiratory assistance device having a plurality of different respiratory assistance modes;
   the input section having a mode input reception unit configured to receive an input of a mode setting for the plurality of different respiratory assistance modes via a display displaying the plurality of different respiratory assistance modes from the patient during operation of the air blower that blows air into the patient's airway;
   the plurality of different respiratory assistance modes including at least one of an undershoot mode and an overshoot mode;
   the control unit having a flow rate control unit configured to, when the mode input reception unit has received the input of the mode setting, control the flow rate or a pressure of the air supplied from the air blower as a reflection of the mode setting of which has been inputted while the air blower is kept operating;
   the input section has a flow rate input reception unit configured to receive an input of a flow rate setting for a prescribed flow rate for the patient from a doctor;
   the input section has a flow rate set permission unit configured to request the doctor to perform a specific input operation when the flow rate input reception unit receives the input of the flow rate setting from the doctor, and to permit the flow rate input reception unit to receive the input of the flow rate setting when the specific input operation satisfies a predetermined condition; and
   the mode input reception unit eliminates a need to perform the specific input operation when the input of the mode setting for the plurality of different respiratory assistance modes is from the patient.

2. The respiratory assistance device according to claim 1, wherein the undershoot mode provides a predetermined pressure decrease time in which the pressure is decreased from a set expiratory reference pressure of the airway pressure by a predetermined pressure decrease width in an expiratory period in which the patient exhales a breath.

3. The respiratory assistance device according to claim 2, wherein the mode input reception unit can independently set the predetermined pressure decrease width and the predetermined pressure decrease time.

4. The respiratory assistance device according to claim 2, wherein the undershoot mode includes a plurality of the undershoot options in which the predetermined pressure decrease widths or the predetermined pressure decrease times are different from each other.

5. The respiratory assistance device according to claim 2, wherein the predetermined pressure decrease time is within 10 seconds.

6. The respiratory assistance device according to claim 1, wherein the overshoot mode provides a predetermined pressure increase time in which the pressure is increased from a set inspiratory reference pressure of the airway pressure by a predetermined pressure increase width in an inspiratory period in which the patient inhales a breath.

7. The respiratory assistance device according to claim 6, wherein the mode input reception unit can independently set the predetermined pressure increase width and the predetermined pressure increase time.

8. The respiratory assistance device according to claim 6, wherein the overshoot mode includes a plurality of the overshoot options in which the predetermined pressure increase widths or the predetermined pressure increase times are different from each other.

9. The respiratory assistance device according to claim 6, wherein the predetermined pressure increase time is within 10 seconds.

10. The respiratory assistance device according to claim 1, wherein:
   the flow rate set permission unit and the flow rate input reception unit are operated during operation of the air blower that blows air into the patient's airway, and
   when the flow rate input reception unit has received the prescribed flow rate, the flow rate control unit controls the flow rate of air supplied from the air blower so as to reflect the prescribed flow rate while the air blower is kept operating.

11. A control method for controlling a respiratory assistance device used during sleep as a continuous positive airway pressure therapy for a patient with sleep apnea syndrome, the respiratory assistance device being connected to a patient's airway and regulating an airway pressure to assist ventilation, the method comprising:
   providing a respiratory assistance program having a plurality of different respiratory assistance modes, the plurality of different respiratory assistance modes including at least one of an undershoot mode and an overshoot mode,
   the respiratory assistance method further comprising:
   a mode input reception step of receiving that receives an input of a mode setting for the plurality of different respiratory assistance modes via a display displaying the plurality of different modes from the patient during operation of an air blower that blows air into the patient's airway, and
   a flow rate control step of, when the mode input reception step of receiving has received the input of the mode setting, controlling a flow rate or a pressure of air supplied from the air blower as a reflection of the mode setting of the plurality of different respiratory assistance modes which has been inputted while the air blower is kept operating;

a flow rate input reception step of receiving an input of flow rate setting for a prescribed flow rate for the patient from a doctor;

a flow rate set permission step of requesting the doctor to perform a specific input operation when the flow rate input reception step receives the input of the flow rate setting from the doctor, and to permit a flow rate input reception unit to receive the input of the flow rate setting when the specific input operation satisfies a predetermined condition; and the mode input reception step of receiving eliminates a need to perform the specific input operation when the input of the mode setting for the respiratory assistance mode is from the patient.

12. The control method according to claim 11, wherein the undershoot mode provides a predetermined pressure decrease time in which the pressure is decreased from a set expiratory reference pressure of the airway pressure by a predetermined pressure decrease width in an expiratory period in which the patient exhales a breath.

13. The control method according to claim 11, wherein the overshoot mode provides a pressure increase time in which the pressure is increased from a set inspiratory reference pressure of the airway pressure by a predetermined pressure increase width in an inspiratory period in which the patient inhales a breath.

14. The control method according to claim 11, wherein
the flow rate set permission step and the flow rate input reception step are performed during operation of the air blower that blows air into the patient's airway, and
when the flow rate input reception step has received the prescribed flow rate, the flow rate control step controls the flow rate of air supplied from the air blower so as to reflect the prescribed flow rate while the air blower is kept operating.

15. A method for controlling a respiratory assistance device used during sleep as a continuous positive airway pressure therapy for a patient with sleep apnea syndrome, the respiratory assistance device being connected to a patient's airway and regulating an airway pressure to assist ventilation, the method comprising:

receiving an input of a mode setting for a plurality of different respiratory assistance modes via a display displaying the plurality of different respiratory assistance modes from the patient during operation of an air blower that blows air into the patient's airway, the plurality of different respiratory assistance modes including at least one of an undershoot mode and an overshoot mode;

controlling a flow rate or a pressure of air supplied from the air blower in response to the mode setting during the step of receiving the input of the mode setting and while the air blower is blowing air into the patient's airway;

receiving an input of a flow rate setting for a prescribed flow rate for the patient from a doctor; and requesting the doctor to perform a specific input operation before allowing the step of receiving the input of the flow rate setting for the prescribed flow rate for the patient from the doctor to thereby permit the step of receiving the input of the flow rate setting for the prescribed flow rate for the patient from the doctor only when the specific input operation satisfies a predetermined condition;

wherein the step of controlling the flow rate or the pressure of air supplied from the air blower in response to the mode setting inputted by the patient does not require input of the specific input operation.

* * * * *